(12) United States Patent
Snoke et al.

(10) Patent No.: US 10,953,159 B2
(45) Date of Patent: *Mar. 23, 2021

(54) ENDOSCOPIC CANNULA

(71) Applicant: URO-1, Inc., Winston-Salem, NC (US)

(72) Inventors: Phillip Jack Snoke, Winston-Salem, NC (US); Philip Morrison Allred, III, Kernersville, NC (US); John Joseph Smith, Winston-Salem, NC (US); Ted Belleza, Watsonville, CA (US)

(73) Assignee: URO-1, Inc., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/564,668

(22) Filed: Sep. 9, 2019

(65) Prior Publication Data

US 2020/0069879 A1 Mar. 5, 2020

Related U.S. Application Data

(63) Continuation-in-part of application No. PCT/US2018/050087, filed on Sep. 7, 2018, which is a continuation of application No. 15/834,333, filed on Dec. 7, 2017, now Pat. No. 10,463,797, and a continuation of application No. 15/697,640, filed on (Continued)

(51) Int. Cl.
| | | |
|---|---|---|
| *A61B 1/307* | (2006.01) | |
| *A61B 1/00* | (2006.01) | |
| *A61M 5/31* | (2006.01) | |
| *A61M 5/315* | (2006.01) | |

(52) U.S. Cl.
CPC ....... *A61M 5/3137* (2013.01); *A61B 1/00135* (2013.01); *A61B 1/307* (2013.01); *A61M 5/3156* (2013.01); *A61M 5/31595* (2013.01); *A61M 2005/3131* (2013.01); *A61M 2205/3379* (2013.01); *A61M 2205/581* (2013.01); *A61M 2205/582* (2013.01); *A61M 2210/1085* (2013.01)

(58) Field of Classification Search
CPC ............... A61B 1/00135; A61B 1/307; A61M 5/31584; A61M 5/3137; A61M 5/3156; A61M 2025/0089; A61M 2025/009; A61M 2025/0037; A61M 25/0041; A61M 25/0084; A61M 2005/3139
See application file for complete search history.

(56) References Cited

U.S. PATENT DOCUMENTS 6,296,633 B1 * 10/2001 Helgerson ......... A61M 25/0009
  606/1
6,855,124 B1 * 2/2005 Gonzalez ........... A61B 17/3478
  604/164.1

(Continued)

*Primary Examiner* — Emily L Schmidt
*Assistant Examiner* — Leah J Swanson
(74) *Attorney, Agent, or Firm* — Wissing Miller LLP

(57) ABSTRACT

A cannula comprising a hollow tube made of a biocompatible, thermoplastic polymer, memory shape material, tipped with an injection needle at it distal end, assumes desired shapes as it distally emerges from a lumen or channel of an instrument such as an introducer or endoscope. The desires shape includes a curvature conforming to an inverse tangent function. The cannula may be supplied alone, with or without an injection needle, and in a sterile pouch, for use with a device of an user's choice that has a suitable lumen or channel to guide the cannula, of the cannula may be used without such an instrument.

20 Claims, 14 Drawing Sheets

Related U.S. Application Data

Sep. 7, 2017, now Pat. No. 10,286,159, application No. 16/564,668, which is a continuation-in-part of application No. 15/834,333, filed on Dec. 7, 2017, now Pat. No. 10,463,797, and a continuation-in-part of application No. 15/722,168, filed on Oct. 2, 2017, now Pat. No. 10,456,164, said application No. 15/834,333 is a continuation-in-part of application No. 15/697,640, filed on Sep. 7, 2017, now Pat. No. 10,286,159.

(56) References Cited

U.S. PATENT DOCUMENTS

| | | | |
|---|---|---|---|
| 10,286,159 B2 * | 5/2019 | Snoke | A61M 5/31581 |
| 2003/0032929 A1 * | 2/2003 | McGuckin, Jr. | A61B 17/3417 |
| | | | 604/272 |
| 2014/0200402 A1 * | 7/2014 | Snoke | A61B 17/42 |
| | | | 600/104 |

* cited by examiner

ENDOSCOPIC CANNULA

REFERENCE TO RELATED APPLICATIONS

This application is a continuation-in-part of each of (a) U.S. patent application Ser. No. 15/722,168 filed Oct. 2, 2017, (b) U.S. patent application Ser. No. 15/834,333 filed Dec. 7, 2017, and (c) International Patent Appl. No. PCT/US18/50087 filed Sep. 7, 2018 published as WO 2019/051315 on Mar. 14, 2019. Said International Patent Appl. claims priority to said U.S. patent application Ser. No. 15/834,333 as well as to U.S. patent application Ser. No. 15/722,168 filed Oct. 2, 2017, and said U.S. patent application Ser. No. 15/834,333 is a continuation-in-part application of U.S. patent application Ser. No. 15/697,640 filed Sep. 7, 2017 and issued as U.S. Pat. No. 10,286,159 on May 14, 2019.

This application incorporates by reference and claims the benefit of the filing date of each of the above-identified patent applications, as well as of the applications that they incorporate by reference, directly or indirectly, and the benefit of which they claim.

FIELD

This patent specification pertains to cannulas used primarily in medical instruments and procedures although they may have non-medical uses as well.

BACKGROUND

Flexible cannulas are widely used in medical procedures to pass through cannula lumens in instruments such as endoscope and introducers and treat internal patient sites, for example to inject a substance in an internal organ, to deliver a substance to an internal site, to apply electrical current or other energy to an internal site, to view an internal organ, and to extract tissue samples or fluids from an internal site, to name a few. Such cannulas may also find use in fields other than medicine, for example to access internal regions in objects that are not otherwise easily reachable.

One condition treated with injections in the bladder Overactive Bladder (OAB). In about 2013, the FDA approved treatment of OAB by periodically injecting OnabotulinumtoxinA (Botox) at sites in a pattern along the inner wall of the patient's bladder. Previous methods of delivering OnabotulinumtoxinA to the bladder have involved inserting a cystoscope in the bladder through the urethra, passing a long metal needle through a lumen or working channel in the cystoscope, and manipulating the entire assembly both laterally and along the axis of the urethra as a unit to inject medication at numerous injection sites in the bladder. Such previous devices and methods have resulted in significant patient discomfort and hold the danger off damage to the urethra and surrounding tissue.

A desired placement and pattern of the multiple injections in the bladder are associated with significantly improved treatment outcomes. It is important that devices and methods of injecting OnabotulinumtoxinA into the bladder offer physicians performing the procedure precise control. However, it had been difficult to create precise injection patterns using such previous devices and methods when the scope moves with the needle when aiming for a new injection site. Moreover, said devices are usually not disposable, and must be disassembled and sterilized after each use, making them difficult to maintain and increasing the risk of contamination or infection. More recently, disposable cannulas with integrated video camera and injection needles have been discussed. See for example US Published Application 2016/0367119 A1 and U.S. Pat. No. 10,278,563.

There are proposals to use cannulas made of shape memory metals that change shape after emerging from lumens in devices such as introducers. See Sachveda U.S. Pat. No. 5,607,435 illustrating in FIG. 4 a tubular section 42 with a leading edge shaped as a surgical needle that curls after exiting a straight delivery tube 50. According to the patent, the curling section is made of metal alloys such as Nitinol. See also McGucken Published Patent Application US 2003/0032929 A1 proposing a shape memory Nitinol infusion needle and mentioning that polymer material might be used in some applications for a shaft in which a shape memory stylet moves but not that the polymer material can be shape memory.

SUMMARY OF THE DISCLOSURE

According to some embodiments, a medical device for insertion into a patient's body and injecting medication into internal tissue comprises: an elongated hollow cannula made of a biocompatible, non-metallic material; and an injection needle protruding distally from a distal end of said cannula. The cannula has a first shape when confined by first external forces acting thereon, and a distal portion that reverts to a second shape when free of said first external forces. The second shape has a predetermined curvature defined by an inverse tangent function and comprising two bends in different directions, and the injection needle is radially spaced from an axis of the first shape when the distal portion of the cannula has reverted to the second shape. The cannula is sufficiently flexible to assume the first shape when in a working channel of an introducer or endoscope but at least the distal portion thereof is sufficiently stiff when in the second shape to force the needle distally into the tissue when a distal force is exerted on a proximal portion of the cannula and/or introducer or endoscope.

At least the distal portion of the cannula of the medical device can have a flexural modulus of about 595,000 psi, and/or the entire cannula have such a flexural modulus. At least the distal portion of said cannula can be made of polyether ether ketone (PEEK), and/or the entire cannula can be a single hollow tube made of PEEK. The medical device can include a working channel configured to exert the first external forces on the cannula, and the cannula can be longer than the working channel such that the distal portion of the cannula protrudes distally from the working channel while a remaining portion of the tube occupies an entire length of the working channel. The two bends of the distal portion of said cannula of the medical device can be spaced from each other by a straight portion of the cannula, and/or the two bends can be in opposite directions.

In some embodiments, a medical device comprises an elongated cannula made of a biocompatible, non-metallic material; the cannula having a first shape when confined by first external forces acting thereon; the cannula having a distal portion that reverts to a second shape when free of said first external forces; and the second shape having a predetermined curvature defined by an inverse tangent function and comprising two bends in different directions. A distal end of the cannula moves radially away from an axis of the first shape as the distal end moves distally away from said first external force At least the distal portion of the cannula of the medical device can have a flexural modulus of about 595,000 psi, and at least the distal portion of the cannula can be made of polyether ether ketone (PEEK). The medical device can further include a working channel configured to exert the first external forces on the cannula when the cannula is therein. The medical device can further include an introducer having the working channel exerting said first external forces on the cannula when therein. The medical device can further include an endoscope having said working channel exerting the first external forces on the cannula when therein. The medical device can further include an injection needle secured to and protruding distally from said distal end of said cannula. The two bends of the distal portion of the tube can be spaced from each other by a straight portion of the tube, and/or the two bends can be in opposite directions.

In some embodiments a method comprises inserting an elongated hollow cannula made of a biocompatible, non-metallic material into a passage in a patient's body while confining at least a distal portion of the cannula to a first shape by first external forces acting thereon; thereafter gradually moving a distal end of the cannula distally from said confining to thereby: cause the distal portion of the cannula to gradually revert to a second shape that has a predetermined curvature defined by an inverse tangent function and comprises two bends in different directions; and cause the distal end to move radially from an axis of said first shape; and injecting medication at selected injection sites of internal tissue of said patient with an injection needle protruding distally from a distal end of the cannula; wherein the injection sites are spaced from each other by distances that depend on a distal distance of said injection needle from said first external forces.

The confining of the method can comprise enclosing the cannula in a working channel of an introducer or endoscope.

DETAILED DESCRIPTION

Figure 1:
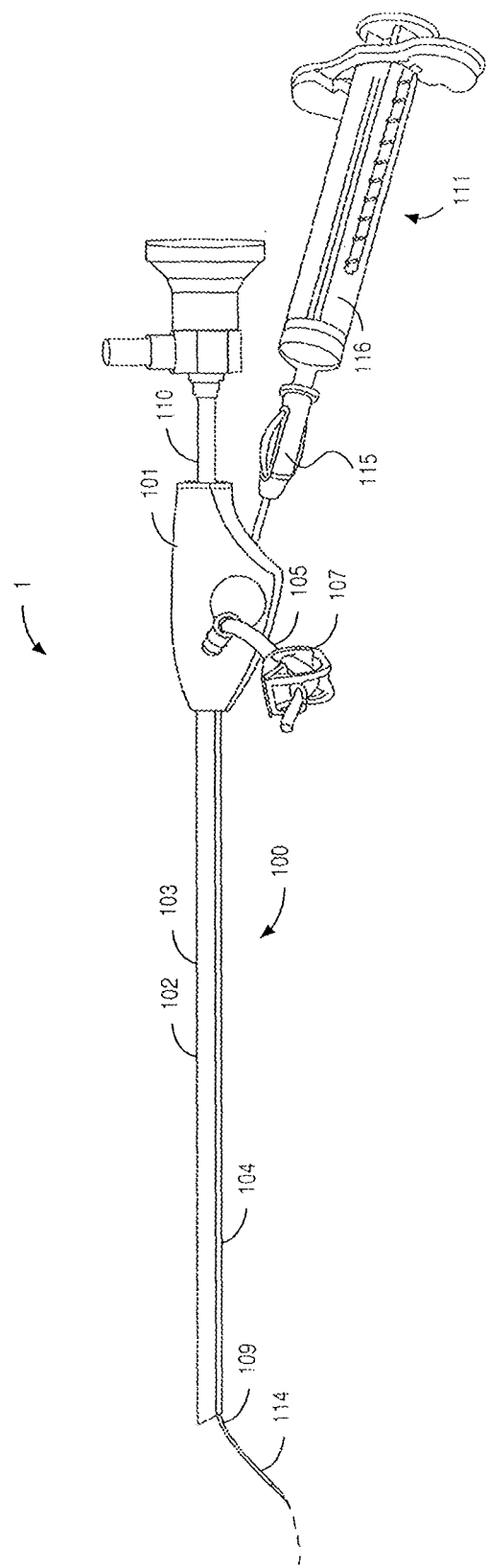
FIG. 1 is a side view of a medical injection assembly, according to some embodiments.

A detailed description of examples of preferred embodiments is provided below. While several embodiments are described, the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all these details. Moreover, for the purpose of clarity, certain technical material that is known in the related art has not been described in detail in order to avoid unnecessarily obscuring the new subject matter described herein. Individual features of one or several of the specific embodiments described herein can be used in combination with features of other described embodiments or with other features. Further, like reference numbers and designations in the various drawings indicate like elements.

This patent specification describes special, hollow, biocompatible polymer cannulas configured to pass through lumens or working channels of a variety of devices and revert to desired predefined curvatures after distally exiting. The lumens of channels can be straight or curved differently from the predefined curvatures to which the polymer cannulas revert when out of those lumens or channels. The lumens or channels can be in any one of a great variety of instruments, including without limitation cystoscopes and other endoscopes of introducers. The curvatures to which the cannulas revert can be as suitable for a specific need or application. The curvature to which a cannula reverts can have a single bend of any desired angle up to 180 degrees relative to a long axis of the cannula, and in some cases can exceed 180 degrees. Another curvature to which a cannula reverts can have two bends in opposite direction, i.e. the curvature can conform to an inverse tangent function. Other curvatures also are possible, e.g., more than two bends, or bends in different planes, etc. The cannulas typically have a distal portion that reverts to the predefined curvatures while the rest of the cannulas are straight or have different curvatures. The cannulas typically have proximal ends that are accessible, for example to inject fluids or other substances into the proximal end of the cannulas or to withdraw substances through the proximal ends. For example, the proximal ends of the cannula can extend proximally from the lumens or working channels for such access.

For use of such cannulas to inject substances at an internal site in a patient, injection needles can be secured to distal tips of the cannulas. For other purposes, such as infusing a substance into or withdrawing a substance from an internal site, the distal tips of the cannulas may be simply open or may be shaped as desired or needed.

The lumens or working channels through which the cannulas pass can be in instruments such as endoscopes, introducers, and other devices that can guide cannulas and allow them to protrude distally from the device. Such devices can include viewing components, such as a video camera and a light source at a distal end, or a scope channel in which a viewing device can be inserted and may include one or more lumens in addition for the lumen or working channel for the cannulas, e.g., fluid passages or working channels for surgical instruments. Alternatively, the devices guiding the cannulas can be simply guides, with no viewing facilities and may or may not have any additional lumens or channels.

One example of such cannulas, as used to inject Botox or other medication into a pattern of injection sides at the inner wall of a patient's bladder, is described in commonly owned U.S. patent application Ser. No. 15/697,640, now U.S. Pat. No. 10,286,159, to which this patent specification claims priority. This patent specification recapitulates that example as illustrative of one use of such cannulas and adds disclosure of other examples of uses of such cannulas.

In the example of treating a patient's bladder with Botox (for OAB) or other medication for other medical conditions, this patent specification highlights the discovery that certain biocompatible polymers can be advantageously configured to inject medication in a desired pattern of sites over a relatively wide area in the interior wall of a bladder with little or no lateral movement of an introducer. This is made possible in part by using a memory shape, biocompatible polymer cannula with a distal portion that revert to a predetermined curvature after exiting a cannula lumen. One particularly important predetermined curvature has two bends in opposite directions. While it may have seemed counterintuitive that such curvatures of a thin, non-metal cannula would provide enough support for a needle to be pushed into tissue and maintain a desired orientation, this curvature has been proved highly useful and has been particularly helpful in injecting at sites arranged over a relatively large area by only rotating and advancing the cannula, with no or only slight side-to-side motion that can harm tissue. Another significant benefit is that the memory shape polymer used for the cannulas described in this patent specification is much less expensive than the metals such as Nitinol that have been traditionally used as memory shape devices. Other benefits are discussed in said patent and further below.

FIG. 1 illustrates a medical injection assembly 1 comprising an introducer 100 that includes a handle 101, a sheath 102, and a scope lumen 103 extending from a first proximal end of the handle 101 to a distal end of the sheath 102, according to some embodiments. The scope lumen 103 is configured to receive an endoscope 110 at the first proximal end of the handle 101 and hold the endoscope in a desired position. A cannula lumen 104 extends from a second proximal end of the handle 101 to the distal end of the sheath 102 and receives a cannula 109 at a second proximal end of the handle 101 and guides the cannula 109 in lumen 104. The introducer 100 may further comprise a fluid line 105 having a distal end in fluid communication with the scope lumen 103 or with a port at the distal end of introducer 100.

Figure 2:
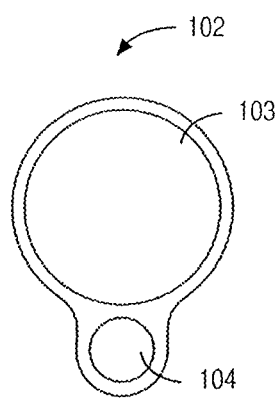
FIG. 2 is a cross-section of a sheath or introducer, according to some embodiments.
Figure 3:
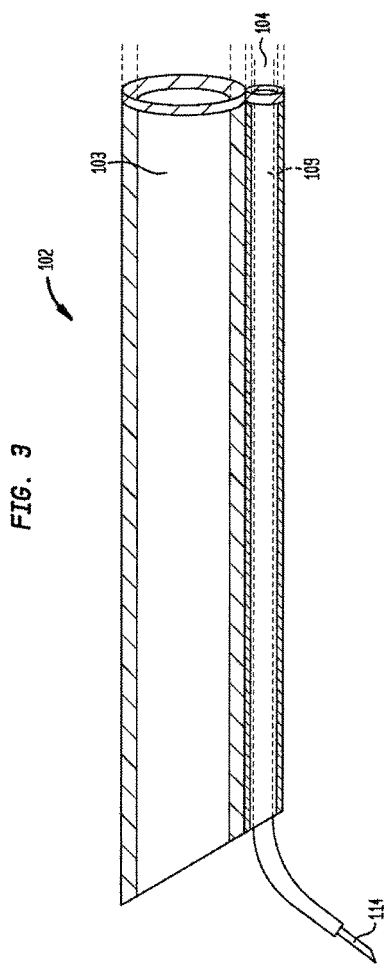
FIG. 3 is a cut-away isometric view of a sheath or introducer, according to some embodiments.

FIGS. 2 and 3 illustrate scope lumen 103 and cannula lumen 104 in sheath 102 of an introducer 100, according to some embodiments. Scope lumen 103 may be configured to receive a variety of endoscopes 110 for illuminating and visualizing target tissue within the body. In some embodiments, the endoscope 110 may be a cystoscope. The inside diameter of the scope lumen 103 preferably fits industry standard cystoscopes known in the art. In preferable embodiments, the scope lumen 103 preferably has an inside diameter of about 4 mm to about 5 mm.

The cannula lumen 104 preferably has an inner diameter of about 1 mm to about 2 mm. The inner diameter or lumen 104 is only slightly more than the outside diameter of cannula 109. The walls of sheath 102 preferably are thin to reduce the outer diameter of the sheath and thereby facilitate passage through a patient's urethra while maintaining strength and rigidity. In preferred embodiments, the sheath walls may have a thickness of about 0.1 mm to about 0.4 mm. The sheath 102 may be comprised of polyether block amides, polyethylene, or other materials with similar rigidity characteristics.

Cannula 109 is a hollow tube made of a biocompatible thermoplastic polymer such as polyether ether-ketone (PEEK), with an outside diameter about 1-2 mm. At least a distal portion of cannula 109 is a shape memory, biocompatible material that reverts to a predetermined curvature after it projects distally from cannula lumen 104. The material and the inside and outside diameters of cannula 109 are carefully selected to meet two mutually exclusive requirements" one is to make the distal portion of cannula 109 stiff so it can help push an injection needle into the inner wall of a patient's bladder when said distal portion is curved, for example in an S-shape, and the other is to make that distal portion of cannula 109 flexible so it can be straight when inside a cannula lumen 104. Preferably, the polymer of cannula 109 has a flexural modulus of about 595,000 psi. Notably, such a flexural modulus allows the user of the device to insert the needle into bladder tissue without causing the cannula to bend or deform in a clinically significant manner. To a skilled person such as a urologist, this means that when injecting in the bladder, the needle would not harm bladder tissue more than has been acceptable in standard-of-care medical practice for conventional injections in the bladder wall and that the visible part of the needle would generally stay in the field of view of a typical endoscope viewing. The bladder wall of adults typically is about 3.5-5.0 mm thick, or an injection needle about 3.0 mm thick would stay in the bladder wall. Some deviation in the needle trajectory during insertion is common and is clinically insignificant so long as it leaves only a temporary tissue disruption, i.e., a disruption that typically clears in a few days, as distinguished from a disruption that punctures the bladder wall or interferes with bladder function for more than a few days. For example, if the cannula deforms so much that the needle cannot penetrate into the bladder wall at a desired injection site or if the cannula bends or deforms so much that the tissue is disrupted to the point of not containing the medication being injected, or if the cannula bends or deforms so much that the needle being forced into tissue opens a slot in tissue rather than a hole about the diameter of the needle, this can be considered a medically significant deformation of the cannula. For example, for a typical adult with a bladder wall thickness about 3.5-5.0 mm, and a 23-gauge injection needle (about 0.58 mm diameter, typically used to inject medication in the bladder wall) that is 3 mm long from the distal tip of the cannula to the sharp point of the needle (again, typical needle length), a deviation in trajectory within 15-20 degrees from the orientation at the start of insertion would not be clinically significant.

Figure 3A:
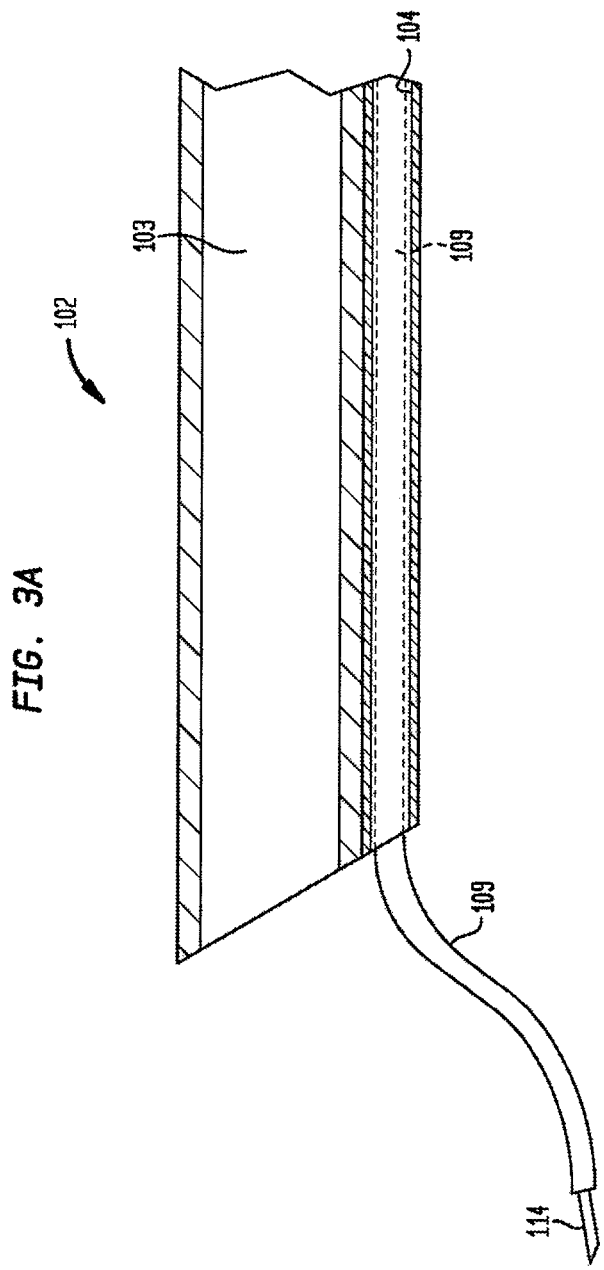
FIG. 3a illustrates a distal portion of a biocompatible polymer cannula that has reverted to a curvature conforming to an inverse tangent function after exiting a distal end of an introducer, according to some embodiments.
Figure 3B:
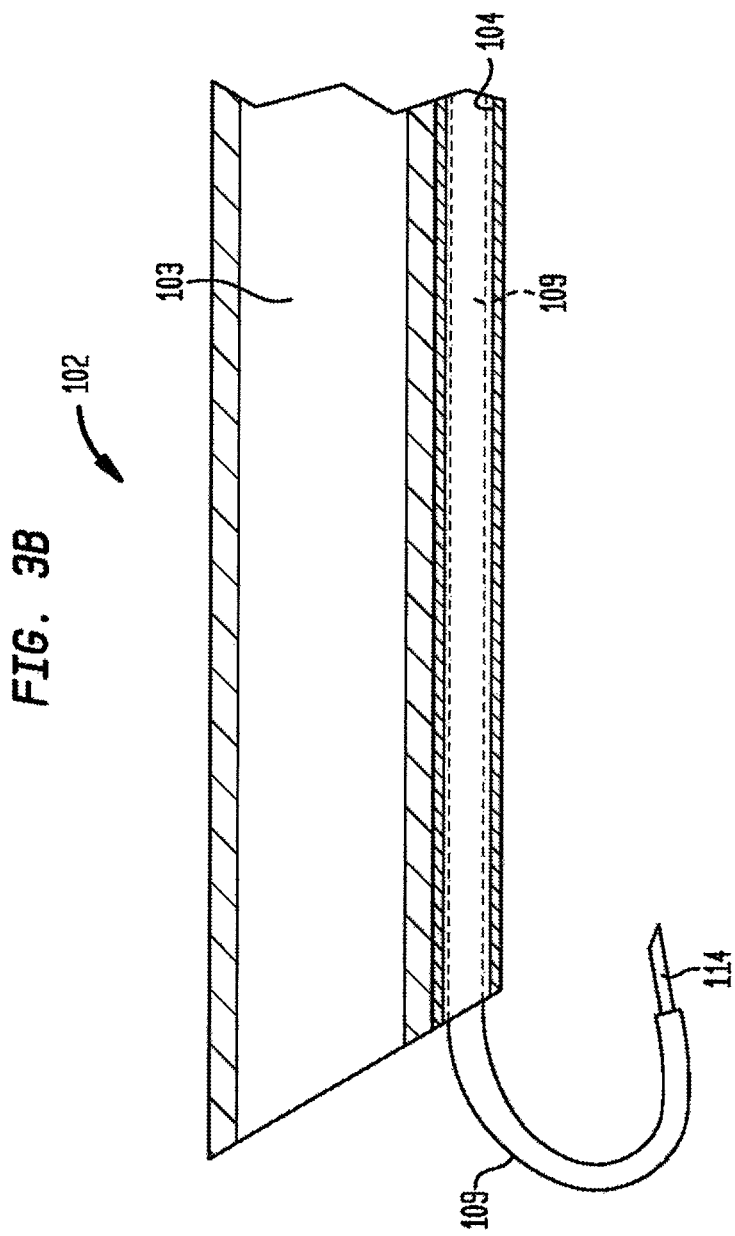
FIG. 3b illustrates a distal portion of a biocompatible polymer cannula that has reverted to a curvature of over 90 degrees after exiting a distal end of an introducer, according to some embodiments.

FIG. 3a illustrates more clearly an example of a desirable curvature of a distal portion of cannula 109 from which injection needle 114 protrudes distally. This curvature conforms to an inverse tangent function. As illustrated, the distant portion of cannula 109, which protrudes distally from the distal end of cannula lumen 104 in introducer 102, has reverted to a curvature that has two bends or inflections in opposite directions and thus can be said to be generally S-shaped. How cannula 109 assumes this curvature is explained below in connection with FIGS. 5A-C. FIG. 3b illustrates an example of an alternative curvature—here the distal portion of cannula 109 that protrudes distally from cannula lumen 104 has reverted to a curvature characterized by a single bend that can be 90 degrees or more and even 180 degrees or more, as may be desirable for a specific medical or other procedure.

Figure 3C:
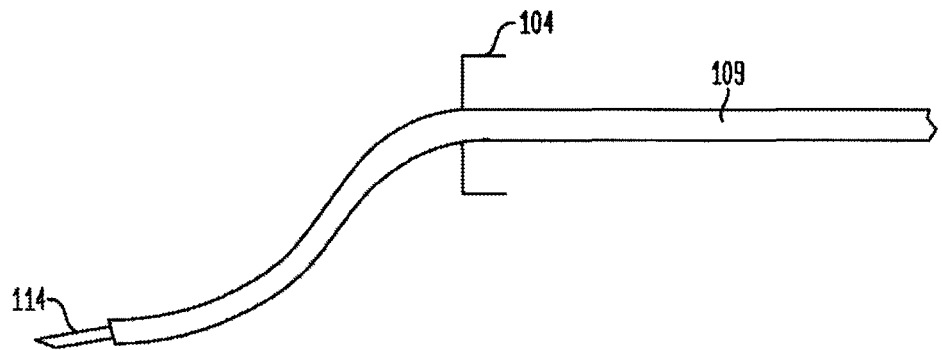
FIG. 3c illustrates a distal portion of a biocompatible polymer cannula that has a curvature conforming to an inverse tangent function and can be used with alternative introducers or endoscopes that have a cannula lumen or a working channel, or by itself, with or without an injection needle at its distal tip, according to some embodiments.
Figure 3D:
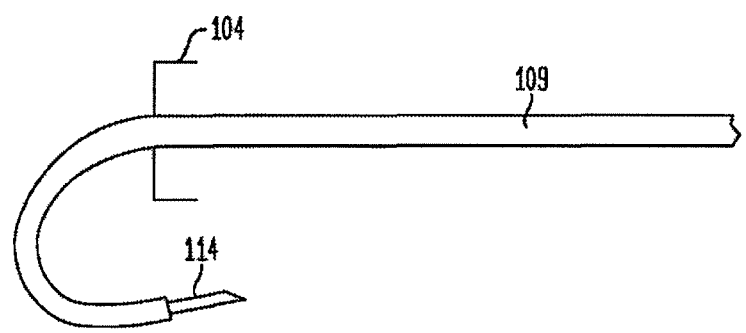
FIG. 3d illustrates a distal portion of a biocompatible polymer cannula that has a curvature of over 90 degrees and can be used with alternative introducers or endoscopes that have a cannula lumen or a working channel, or by itself, with or without an injection needle at its distal tip, according to some embodiments.
Figure 3E:
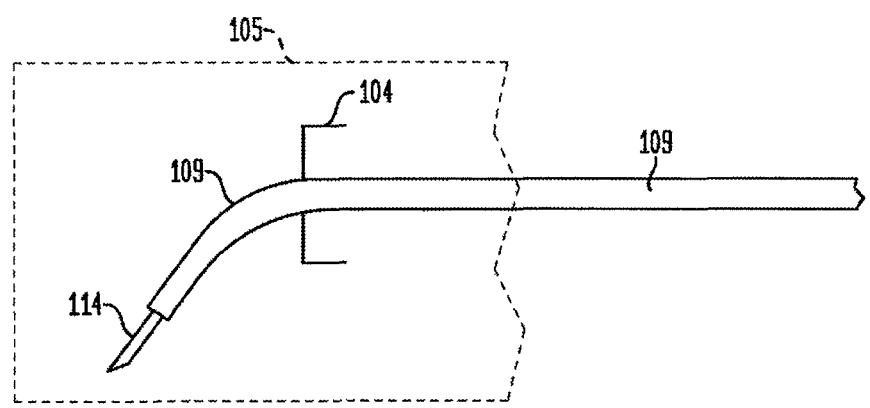
FIG. 3e illustrates a distal portion of a biocompatible polymer cannula that has a curvature of less than 90 degrees and can be used with alternative introducers or endoscopes that have a cannula lumen or a working channel, or by itself, with or without an injection needle at its distal tip, according to some embodiments.

FIGS. 3c-e illustrate cannula 109 as in may be used alone or with any one of a variety of instruments that can guide it and from which it can emerge distally to revert to a predetermined curvature. An injection needle 114 can be secured at the cannula's distal tip or the cannula can be used without such a needle. Cannula 109 shown in FIGS. 3c-e can be supplied to users alone, with or without an injection needle 114 at its tip. Preferably, cannula 109, with or without needle 114, would be supplied in a sterile package that the user can open when needed and use the cannula as desired. As non-limiting examples, a user may pass cannula 109, with or without needle 114, through a lumen or working channel of a device such as an introducer or an endoscope or some other guide. Reference numeral 104 schematically illustrates any one of such variety of instruments that may be the same or different from introducer 100 shown in FIG. 1-3b. As other non-limiting examples, a user may use the cannula of FIGS. 3c-3e without an introducer and with or without a needle.

In each of FIGS. 3c-3e, cannula 109 is a hollow tube of a shape memory, biocompatible polymer. Several different predetermined curvatures to which a distal portion of the cannula reverts are illustrated. In FIG. 3c, the curvature conforms to an inverse tangent function; in FIG. 3d, the curvature is a bend that is over 180 degrees but can be any angle up to an even exceeding 180 degrees; and in FIG. 3e the curvature is a single bend.

FIG. 3e schematically illustrates a sterile package 105 enclosing cannula 109; like sterile packages can enclose the cannulas of FIGS. 3c and 3d. In each case, a needle 114 may be secured to the cannula or may be absent. In some embodiments, the entire instrument illustrated in FIG. 1 may be delivered to a user enclosed in a like sterile pouch, typically without syringe 111.

The cannula 109 that has been used in a medical procedure typically is discarded as medical grade waste rather than being sterilized and used in another procedure to thereby eliminate or reduce the danger of possible contamination in other procedures.

The predefined curvatures discussed above exist when the cannula is free of external forces that would prevent it from assuming such curvatures. When subjected to external forces, such as when confined in a straight lumen or working channel, the cannula would extend along a straight axis if the lumen or channel is straight or would assume the curvature of the lumen or channel that is not straight.

Figure 4:
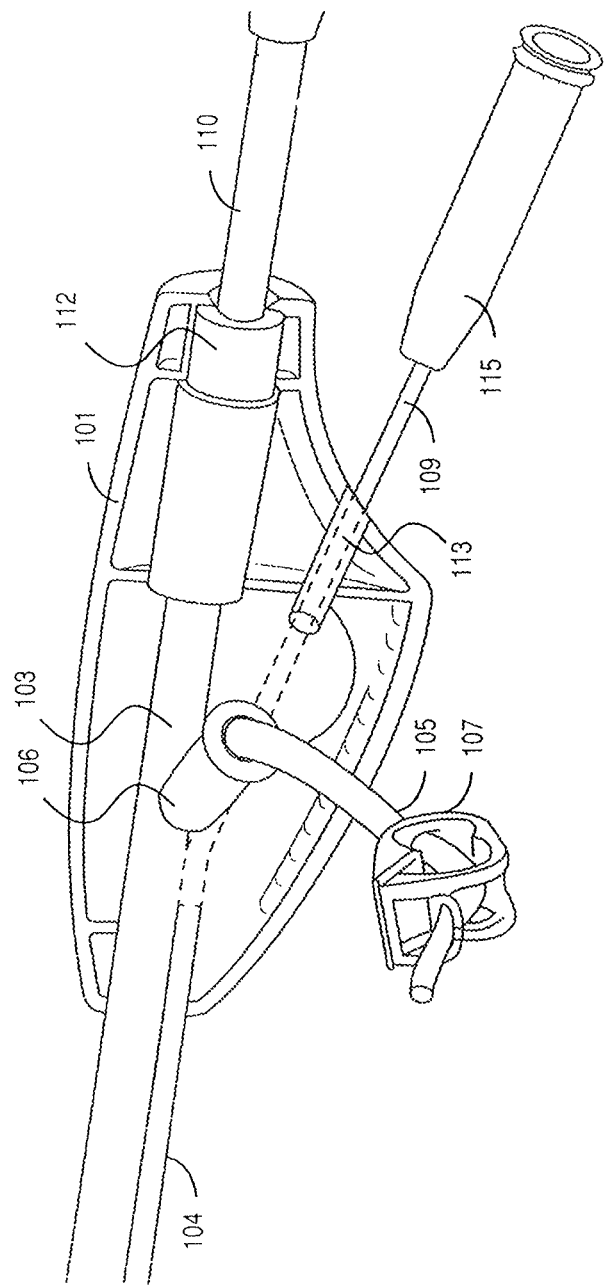
FIG. 4 is a cross-section of a handle of an introducer, according to some embodiments.

Returning to the example of using the cannula to inject medication in a patient's bladder, FIG. 4 illustrates handle 101 of an introducer 100 according to some embodiments. A scope lumen 103 extends from a proximal end of the handle 101 and may be configured to receive an endoscope 110 from a proximal end of the handle 101. A scope seal 112 is positioned at a proximal end of the handle 101 to engage endoscope 110. The scope seal 112 is a material with an appropriate coefficient of friction to hold endoscope 110 in place. The scope seal 112 preferably comprises silicone.

The cannula lumen 104 extends from a proximal end of the handle 101 and is configured to receive cannula 109 from a proximal end of the handle 101. A cannula seal 113 is at a proximal end of the handle 101 to engage cannula 109. The cannula seal 113 preferably is made of a material with an appropriate coefficient of friction to hold a cannula 109 in place. The material of the cannula seal 113 preferably comprises silicone. The handle 101 further comprises a fluid line 105 in fluid communication with the scope lumen 103. The distal end of the fluid line 105 connects to the scope lumen 103 via a watertight fluid connector. In yet other embodiments, the distal end of the fluid line 105 may be integrated directly into the scope lumen 103 via known manufacturing methods such as various molding techniques, welding, 3D printing, adhesives, etc. The fluid line 105 may comprise a second fluid connector 106. In preferred embodiments, the second fluid connector 106 may be a luer lock. The fluid line 105 may further comprise a pinch valve 107. The pinch valve 107 may control the flow of fluid form a fluid source through the fluid line 105 and into the scope lumen. A port at the distal end of the scope lumen can be provided for outflow or inflow of fluid. FIG. 4 further illustrates a fluid connector 115 coupled to a proximal end of cannula 109 and provided with a pinch valve 113 to selectively deliver fluids into cannula 109 for injecting through needle 114.

The needle 114 may be a commercially available hypodermic needle suitable for performing injections of OnabotulinumtoxinA or other desirable medication. The outer diameter of the needle 114 is slightly less than the diameter of the cannula 109, so that the needle can be friction-fitted in the cannula. For example, the needle 114 may be a 23-gauge needle and may extend past the cannula 109 about 1.0 mm to about 3.0 mm in length. In such configurations, the distal tip of the cannula 109 acts as a circumferential wall that helps keep the needle 114 from penetrating into the target tissue past the distal tip of the cannula 109.

Figure 5A:
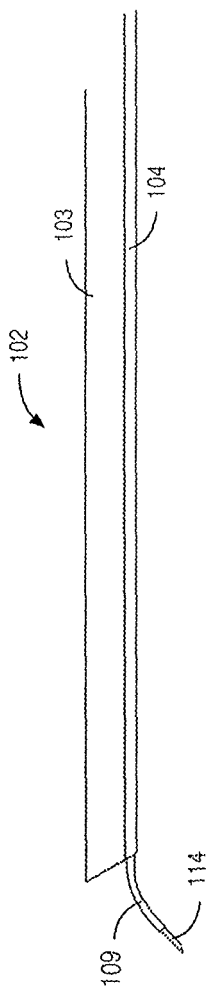
FIG. 5A is a side view of a cannula exiting a sheath or introducer, according to some embodiments.
Figure 5B:
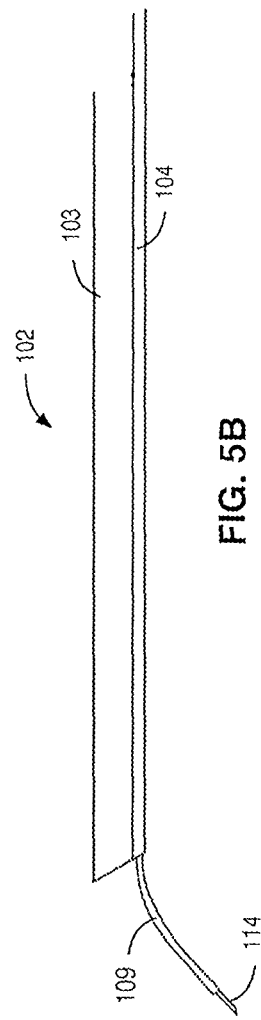
FIG. 5B is a side view of a cannula exiting a sheath or introducer, according to some embodiments.
Figure 5C:
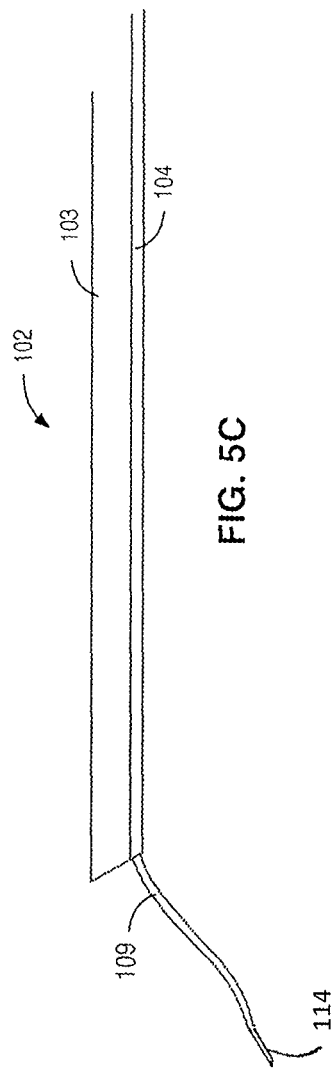
FIG. 5C is a side view of a cannula exiting a sheath or introducer, according to some embodiments.

FIGS. 5A-5C illustrate how a cannula 109, with a needle 114 attached to its distal tip, changes it curvature as it moves distally in cannula lumen 104 such a distal portion of the cannula protrudes distally from the cannula lumen. When the distal portion of cannula 109 is entirely within the cannula lumen, the cannula assumes the shape dictated by the external forces the cannula lumen exerts. If the cannula lumen is straight, so is the distal portion of the cannula while entirely in the cannula lumen. However, when the cannula 109 is made of the shape memory biocompatible polymer discussed above, as the distal portion of the cannula starts emerging distally from cannula lumen 104, the part of the cannula that has emerged starts reverting to its predetermined shape. FIG. 5A illustrates an early stage, in which a relatively short length of cannula 109 has emerged and has reverted to a curvature of a single bend down. FIG. 5B illustrates a stage in which a greater length of cannula 109 has emerged and still has only a single bend. FIG. 5C illustrates a stage in which the entire desired distal portion of cannula 109 is out of cannula lumen 104 and has reverted to a predetermined shape conforming to an inverse tangent function, with two bends of inflections in opposite directions.

The vertical distance between the distal tip of cannula 109 and a long axis of cannula lumen 104 changes in the course of movement of cannula 109 distally out of cannula lumen 104. This distance is relatively small in FIG. 5A, greater in FIG. 5B, and greatest in FIG. 5C. One benefit of this feature is discussed in connection with FIGS. 8A-B.

Figure 6:
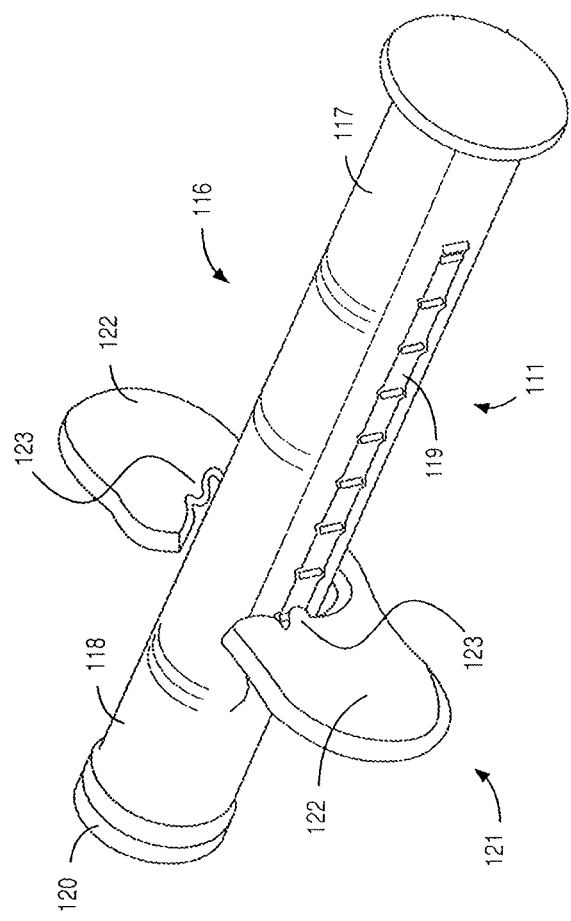
FIG. 6 is an isometric view of a plunger body, according to some embodiments.
Figure 7:
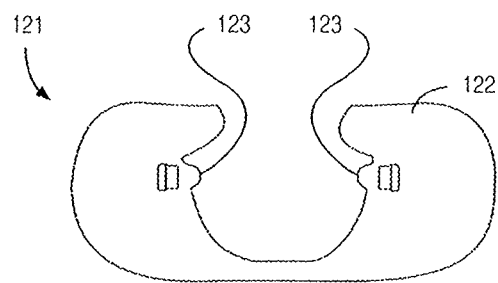
FIG. 7 is a bird's eye view of a finger grip, according to some embodiments.

FIGS. 6-7 illustrate a syringe 111 that can be coupled to fluid connector 115 for delivery of fluid such as medication for injection in a patient's bladder through cannula 109 and needle 114. Syringe 111 comprises a syringe barrel (not seen in these FIGS.) and a plunger body 116 having a first portion 117 proximate the proximal end and second portion 118 proximate the distal end, wherein the first portion 117 has a plurality of corresponding detents 119 on opposite sides of the first portion 117. The syringe 111 may also comprise a sealing cap 120 attached to the distal end of the plunger body 116 and a finger grip 121 comprising two paddles 122. The finger grip may be configured to be removably coupled to the plunger body 116 and to interact with the detents 119 to provide audible and tactile feedback to a user when the plunger body 116 is pushed through the finger grip 121 in a distal direction. The second portion 118 may fit into commercially available syringe barrels with the sealing cap 120 forming a watertight seal within the syringe barrel. In preferred embodiments, commercially available 10 cc syringe barrels may be used. The finger grip 121 may be configured to clip on to the plunger body 116. The finger grip 121 may include tabs 123 on the interior of both paddles 122. The tabs 123 may fit into grooves between the detents 119 on the first portion 117. When the user pushes the plunger body 116 in a distal direction into the syringe barrel, the detents 119 provide resistance against the movement until the tabs 123 bend enough to clear a set of detents 119 and fit into the next set of grooves. The detents 119 may be spaced along the first portion 117 such that clearing one set of detents 119 results in an ejection of a specific amount of fluid from the syringe. In preferred embodiments, clearing one set of detents would result in the ejection of 1 cc of fluid from the syringe. When the user causes tabs 123 to clear a set of detents 119 and the tabs 123 come to rest in the subsequent grooves, the user is provided with tactile and audible feedback to indicate that one such predetermined unit of fluid has been ejected from the syringe.

Figure 7A:
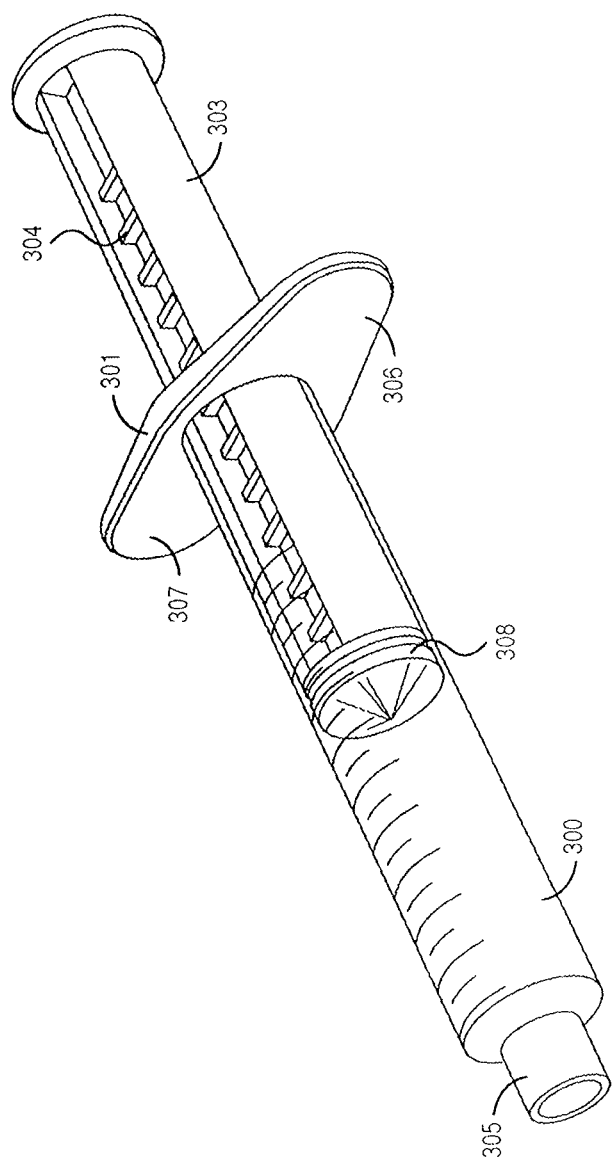
FIGS. 7a and 7b are two perspective views from different viewpoints that illustrate another example of a syringe that can be coupled to a fluid connector.
Figure 7B:
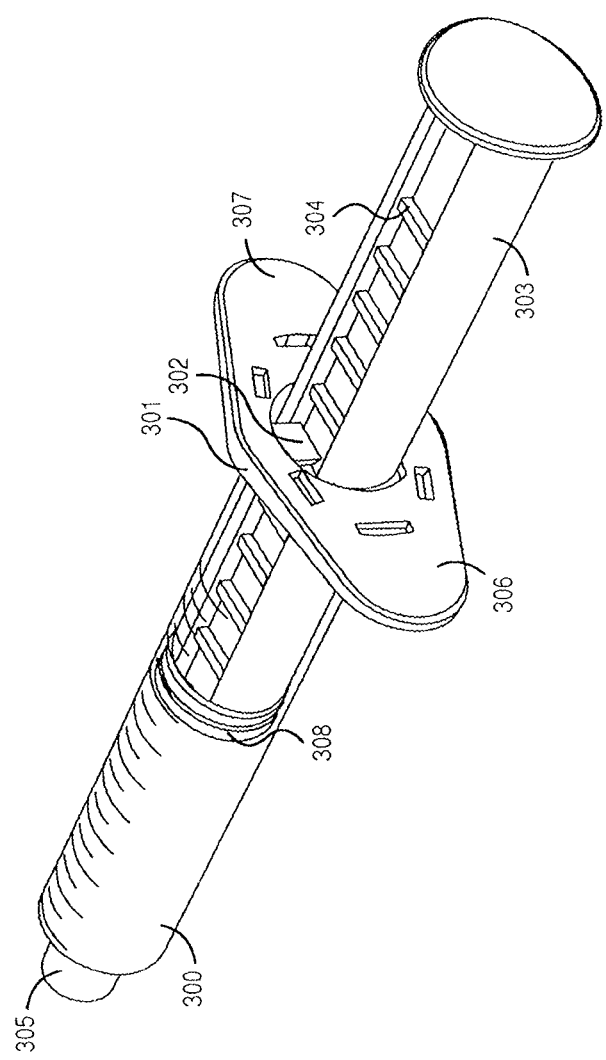

FIGS. 7a and 7b are two perspective views from different viewpoints that illustrate another example of a syringe that can be coupled to fluid connector 115. A syringe barrel 300 has a coupler 305 at a distal end that is shaped and dimensioned to fit connector 115 and a finger hold 301 at a proximal end that has a paddles or wings 306, 307 and a flexible tab 302. A plunger body 303 slides in barrel 300 and has at its distal end a cap 308 that forms a seal against the inside wall of barrel 300. Plunger body 303 has detents 304 along at least one of its long walls that flexible tab 302 engages as the plunger body moves relative to the barrel.

Figure 8A:
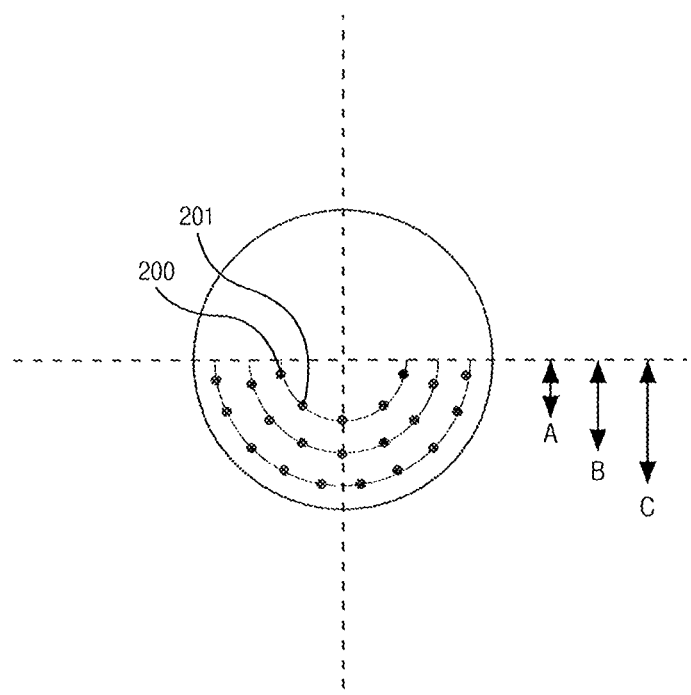
FIG. 8A is a frontal view diagram of a bladder injection pattern, according to some embodiments.
Figure 8B:
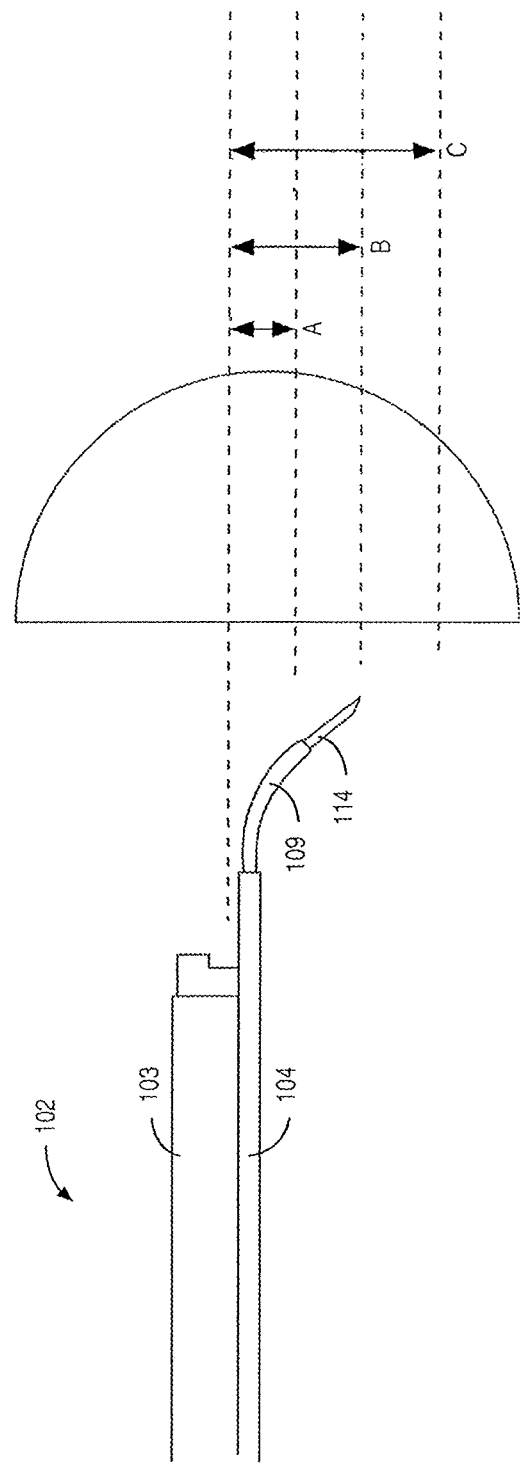
FIG. 8B is a side view diagram of a bladder injection pattern, according to some embodiments.

FIGS. 8A-8B illustrate therapeutically effective patterns of injection sites according some embodiments. It has been found beneficial to disperse the injections of medication such as OnabotulinumtoxinA across the bladder tissue. In preferred embodiments, injections patterns may comprise three concentric semi-circles in the lower half of the bladder with radii A, B, and C. Such an injection pattern may be created by moving the cannula 109 distally until the needle 114 is at a distance A from the long axis of the sheath 102 of the introducer 100 and rotating one or both of introducer 100 and cannula 109 until the needle 114 is at injection site 200. The introducer 100 and/or cannula 109 are then moved distally to penetrate the bladder's inner wall with injection needle 114 and inject OnabotulinumtoxinA or other medication. The needle 114 is then withdrawn from the bladder wall by proximally moving cannula 109 alone or together with introducer 100 and the introducer and/or the cannula are rotated about the long axis of the introducer until the needle 114 is at injection site 201, and the injection process is repeated. Once the injection pattern for the semi-circle with radius A is complete, the cannula 109 may be moved distally relative to introducer 100 (and the introducer may be moved proximally or distally as needed) until the needle 114 is at a distance B from the axis defined by the sheath 102 of the introducer 100, and the previous steps can be repeated to create the injection patterns for the semi-circles with radii B and C. Preferably, A is approximately 0.43 inches, B is approximately 0.8 inches, and C is approximately 1.2 inches. By rotating the introducer 100 and/or cannula 109 about the introducer's long axis to position the needle rather than moving the introducer 100 laterally or pivoting it about an axis transverse to the long axis, the patient experiences less discomfort and possible injury from stretching of the urethra.

A method for treating overactive bladder comprises inserting an endoscope 110 into a scope lumen 103 of an introducer 100, according to some embodiments. The method may further comprise inserting a cannula 109 into a cannula lumen 104 of the introducer 100, the cannula 109 configured such that the distance between the distal tip of the cannula 109 and the axis defined by the sheath 102 of the introducer 100 increases as the cannula 109 is moved in a distal direction out of the introducer, wherein a syringe 111 filled with OnabotulinumtoxinA or other medication is coupled to the proximal end of the cannula 109. The method may further comprise guiding the introducer 100 through the urethra of a patient to the patient's bladder. The method may further include extending the distal portion of the cannula 109 past the distal end of the introducer 100 until a needle 114 attached to the distal end of the cannula 109 is placed at a desired radial distance from the long axis defined by the sheath of the introducer. The method may further comprise rotating the introducer 100 and/or cannula 119 to position the needle 114 at a desired position. The method may further comprise moving the introducer and/or the cannula in a distal direction to insert the needle 114 into the bladder. The method may further include activating the syringe 111 to inject OnabotulinumtoxinA or other medication into the bladder. The method may further include moving the introducer 100 and/or the cannula 109 in a proximal direction to withdraw the needle 114 from the bladder. The method may further include repeating the extending, rotating, moving distally, activating, and moving proximally steps until a therapeutically effective amount of OnabotulinumtoxinA or other medication has been injected in a therapeutically effective pattern into the bladder.

An alternative method comprises enclosing a cannula 109, with or without an injection needle 114, in a sterile pouch and delivering the pouch to a user. The method further comprised opening the sterile pouch and passing the cannula through a lumen or channel of a device such as an introducer, endoscope or some other guide that may or may not be already inserted into a patient's cavity. The method further comprises advancing the cannula distally until a distal portion thereof starts protruding distally from such lumen or channel and begins to revert to its predetermined curvature. The method further includes advancing the cannula distally even more relative to a distal end of the lumen or channel, so more of the distal portion of the cannula reverts to its predetermined shape, and using the cannula such as to inject a substance into a patient's bladder or deliver or inject a substance into another body cavity. The cannula is them withdrawn from the patient, alone or together with the instrument through which it passed, and the cannula 109 is discarded along with any needle 114 as medical grade waste.

Although the foregoing has been described in some detail for purposes of clarity, it will be apparent that certain changes and modifications may be made without departing from the principles thereof. There can be many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims. Numerous specific details are described to provide a thorough understanding of the disclosure. However, in certain instances, well-known or conventional details are omitted to avoid obscuring the description.

The invention claimed is:

1. A medical device for insertion into a patient's body and injecting medication into internal tissue, said device comprising:
   an elongated hollow cannula made of a biocompatible, non-metallic material;
   an injection needle protruding distally from a distal end of said cannula;
   said cannula having a first shape when confined by first external forces acting thereon;
   said cannula having a distal portion that reverts to a second shape when free of said first external forces;
   said second shape having a predetermined curvature defined by an inverse tangent function and comprising two bends in different directions;
   whereby said injection needle is radially spaced from an axis of said first shape when said distal portion of the cannula has reverted to said second shape; and
   wherein said cannula is sufficiently flexible to assume said first shape when in a working channel of an introducer or endoscope but at least said distal portion thereof has a flexural modulus sufficient for inserting the injection needle distally into bladder wall when said distal portion of the cannula has reverted to said predetermined curvature.

2. The device of claim 1, in which at least said distal portion of said cannula has a flexural modulus of about 595,000 psi.

3. The device of claim 2, in which at least one portion of the cannula in addition to said distal portion has said flexural modulus.

4. The device of claim 1, in which at least said distal portion of said cannula is made of polyether ether ketone (PEEK).

5. The device of claim 4, in which the cannula is a single hollow tube made of PEEK.

6. The device of claim 1, further including a working channel configured to exert said first external forces on said cannula.

7. The device of claim 6, wherein said cannula is longer than said working channel such that said distal portion of the cannula protrudes distally from the working channel while a remaining portion of the cannula occupies an entire length of the working channel.

8. The device of claim 1, in which said two bends of the distal portion of said cannula are spaced from each other by a straight portion of the cannula.

9. The device of claim 1, in which said two bends are in opposite directions.

10. A medical device comprising:
    an elongated cannula made of a biocompatible, non-metallic material;
    said cannula having a first shape when confined by first external forces acting thereon;
    said cannula having a distal portion that reverts to a second shape when free of said first external forces; and
    said second shape having a predetermined curvature defined by an inverse tangent function and comprising two bends in different directions;
    whereby a distal end of said cannula moves radially away from an axis of said first shape as said distal end moves distally away from said first external forces; and
    wherein at least said distal portion of the cannula has a flexural modulus sufficient for inserting an injection needle protruding from a distal end of the cannula into bladder wall when said distal portion has reverted to said predetermined curvature.

11. The device of claim 10, in which at least said distal portion of said cannula has a flexural modulus of about 595,000 psi.

12. The device of claim 11, in which at least said distal portion of said cannula is made of polyether ether ketone (PEEK).

13. The device of claim 10, further including a working channel configured to exert said first external forces on said cannula when the cannula is therein.

14. The device of claim 13, further comprising an introducer having said working channel exerting said first external forces on the cannula when therein.

15. The device of claim 13, further comprising an endoscope having said working channel exerting said first external forces on the cannula when therein.

16. The device of claim 10, further comprising an injection needle secured to and protruding distally from said distal end of said cannula.

17. The device of claim 10, in which said two bends of the distal portion of said cannula are spaced from each other by a straight portion of the tube.

18. The device of claim 10, in which said two bends are in opposite directions.

19. A method comprising:
    inserting an elongated hollow cannula having a selected flexural modulus and made of a biocompatible, non-metallic material into a passage in a patient's body while confining at least a distal portion of said cannula to a first shape by first external forces acting thereon;
    thereafter gradually moving a distal end of said cannula distally from said confining to thereby:
    cause said distal portion of said cannula to gradually revert to a second shape that has a predetermined curvature defined by an inverse tangent function and comprises two bends in different directions, wherein said selected flexural modulus is sufficient for inserting a needle at a distal end of said cannula into a patient's bladder wall when said distal portion of the cannula has reverted to said predetermined curvature; and
    cause said distal end to move radially from an axis of said first shape; and
    injecting medication at selected injection sites of internal tissue of said patient with an injection needle protruding distally from a distal end of said cannula;

wherein said injection sites are spaced from each other by distances that depend on a distal distance of said injection needle from said first external forces.

20. The method of claim 19, wherein said confining comprises enclosing said cannula in a working channel of an introducer or endoscope.

\* \* \* \* \*